US00PP09354P

United States Patent [19]

Hope

[11] Patent Number: Plant 9,354

[45] Date of Patent: Oct. 31, 1995

[54] KALANCHOE PLANT NAMED 'MAYA'

[75] Inventor: Claude Hope, Cartago, Costa Rica

[73] Assignee: Ball Seed Co., a Division of Geo. J. Ball, Inc., West Chicago, Ill.

[21] Appl. No.: 380,601

[22] Filed: Jan. 30, 1995

[51] Int. Cl.[6] ..... A01H 5/00

[52] U.S. Cl. ..... Plt./87.15

[58] Field of Search ..... Plt./87.15

*Primary Examiner*—James R. Feyrer
*Attorney, Agent, or Firm*—C. A. Whealy

[57] ABSTRACT

A distinct cultivar of Kalanchoe plant named Maya, characterized by its moderately vigorous growth habit; freely branching habit; proportional leaf size; peduncles that do not stretch during flowering or during postproduction; soft red flower color; and excellent keeping quality.

1 Drawing Sheet

The present invention relates to a new and distinctive cultivar of Kalanchoe plant, botanically known as *Kalanchoe blossfeldiana,* and hereinafter referred to by the cultivar name Maya.

The new cultivar is a product of a planned breeding program conducted by the inventor in Cartago, Costa Rica.

The new cultivar originated from a cross made by the inventor of the nonpatented cultivar Sonata as the male or pollen parent with the proprietary selection KLV 80-22P as the female or seed parent.

The cultivar Maya was discovered and selected by the inventor as a flowering plant within the progeny of the stated cross in a controlled environment in Cartago, Costa Rica. Asexual reproduction of the new cultivar by terminal cuttings taken at Cartago, Costa Rica, and subsequently at West Chicago, Ill., has shown that the unique features of this new Kalanchoe are stabilized and reproduced true to type in successive generations of asexual reproduction.

The cultivar Maya has not been observed under all possible environmental conditions. The phenotype may vary somewhat with variations in environment such as temperature, daylength and light intensity, without, however, any variance in genotype. The following observations, measurements and comparisons describe plants grown in West Chicago, Ill., under commercial practice in a glass-covered greenhouse.

The following traits have been repeatedly observed and are determined to be the unique characteristics of Maya. These characteristics in combination distinguish Maya as a new and distinct cultivar:

1. Moderately vigorous plant growth habit.
2. Freely branching habit, plants do not require pinching.
3. Proportional leaf size to plant size.
4. Peduncles do not stretch during flowering or during postproduction.
5. Soft red petal color.
6. Long-lasting keeping quality. Flowers do not fade and foliage maintains good color for seven weeks under interior conditions.

The new Kalanchoe differs from its parents in the color of the petals. The petal color of the male parent, Sonata, is salmon orange; and the petal color of the female parent, selection KLV 80-22P, is yellow in contrast to the soft red color of Maya petals. In addition the cultivar Sonata flowers two weeks later than the cultivar Maya; and selection KLV 80-22P is more upright and vigorous compared to the cultivar Maya.

Maya is most similar to the nonpatented Kalanchoe cultivar Tico Red Velvet in the following characteristics:

1. Plants of Maya are more vigorous than plants of Tico Red Velvet.
2. Leaves of Maya are larger than leaves to Tico Red Velvet.
3. Plants of Maya have more flowers per main cyme than plants of Tico Red Velvet.
4. Petals of plants of Maya are broader than petals of Tico Red Velvet.
5. Petal color of Maya is soft red compared to cherry red color of petals of Tico Red Velvet.
6. Plants of Maya maintain flower and foliage color for an average of one week longer than plants of Tico Red Velvet in the interior environment.

The accompanying colored photograph illustrates the overall appearance of the new cultivar, showing the colors as true as it is reasonably possible to obtain in colored reproductions of this type. The photograph comprises a top perspective view of a typical potted plant of Maya.

In the following description, color references are made to The Royal Horticultural Society Colour Chart except where general terms of ordinary dictionary significance are used. Measurements and numerical values represent averages for eight typical plants.

Botanical classification: *Kalanchoe blossfeldiana* cultivar Maya.

Parentage:

*Male.*—Nonpatented cultivar Sonata.

*Female.*—Proprietary selection KLV 80-22P.

Propagation:

A. *Type cutting.*—Terminal cuttings.

B. *Time to initiate roots.*—7 days at 25° C. soil temperature.

C. *Rooting habit.*—Fine, fibrous, and well-branched.

Plant description:

A. *Form.*—Upright and moderately compact.

B. *habit of growth.*—Freely branching.

C. *Plant height at flowering.*—22 cm.

D. *Foliage description.*—1. Size: a. Length: 12 cm. b. Width: 8 cm. 2. Shape: Ovate. 3. Texture: Succulent. 4. Margin: Crenate. 5. Color: a. Young foliage top side: 147A. b. Young foliage under side: 147B. c. Mature foliage top side: 147A. d. Mature foliage under side: 147B. e. Leaf margin: 59A.

E. *Stem description.*—1. Main stem diameter: 0.9 cm. 2. Color: 147B.

Flower description:

A. *Flower type and habit.*—Freely flowering, flowers arranged in panicles, cymose.

B. *natural flowering season.*—Autumn/winter in Northern Hemisphere. Flower initiation and development can be induced under short day/long night conditions.

C. *Flowers borne.*—Above foliage, arising from leaf axils.

D. *Quantity of flowers.*—40 on lateral cymes, 100 on main cyme.

E. *Petals.*—1. Shape: Elliptic. 2. Base: Linear. 3. Tip: Acute. 4. Size: a. Length: 1.4 cm. b. Width: 1.2 cm. 5. Color: a. When opening: 50A. b. Mature, top side: 50A. c. Mature, under side: 50B. d. Fading to: 50A. e. Peduncle: 147B.

F. *Reproductive organs.*—1. Stamens: a. Stamen number: 8. b. Anther color: 143B. c. Pollen color: 5B. 2. Pistils: a. Stigma color: 3C. b. Style color: 143B. c. Ovary number: 4. d. Ovary size: Length: 5 mm. Width: 1 mm. e. Ovary color: 143B.

Disease resistance: No fungal, bacterial nor viral problems observed.

Seed production: Seed production has not be observed.

I claim:

1. A new and distinct cultivar of Kalanchoe plant named Maya, as illustrated and described.

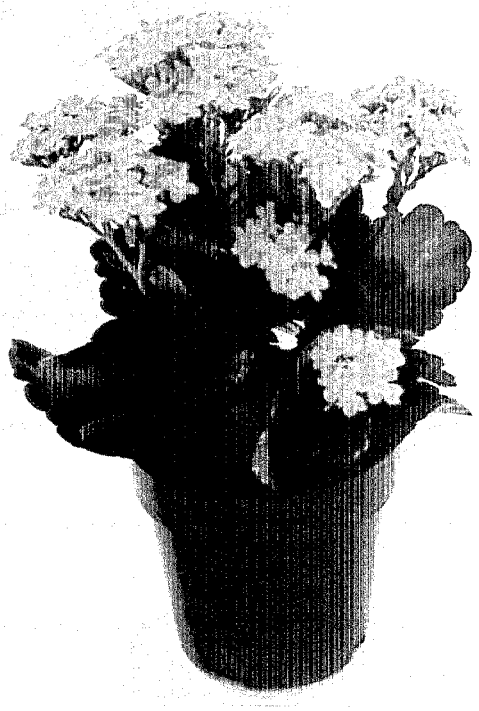

* * * * *